US008911996B2

(12) United States Patent
Srouji et al.

(10) Patent No.: US 8,911,996 B2
(45) Date of Patent: Dec. 16, 2014

(54) ELECTROSPUN SCAFFOLDS AND METHODS OF GENERATING AND USING SAME

(75) Inventors: Samer Srouji, Haifa (IL); Eyal Zussman, Haifa (IL); Erella Livne, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 1213 days.

(21) Appl. No.: 12/449,262

(22) PCT Filed: Jan. 31, 2008

(86) PCT No.: PCT/IL2008/000134
§ 371 (c)(1),
(2), (4) Date: Mar. 8, 2010

(87) PCT Pub. No.: WO2008/093341
PCT Pub. Date: Aug. 7, 2008

(65) Prior Publication Data
US 2010/0172952 A1 Jul. 8, 2010

Related U.S. Application Data
(60) Provisional application No. 60/898,394, filed on Jan. 31, 2007.

(51) Int. Cl.
C12N 5/0793 (2010.01)
C07K 14/00 (2006.01)
A61L 27/56 (2006.01)
A61L 27/46 (2006.01)

(52) U.S. Cl.
CPC ............ *A61L 27/56* (2013.01); *A61L 2400/12* (2013.01); *A61L 27/46* (2013.01); *Y10S 977/795* (2013.01)
USPC ........................... 435/398; 514/16.7; 977/795

(58) Field of Classification Search
None
See application file for complete search history.

(56) References Cited

U.S. PATENT DOCUMENTS

2006/0154063 A1  7/2006  Fujihara et al.
2011/0276147 A1*  11/2011  Cook et al. .................. 623/23.51

FOREIGN PATENT DOCUMENTS

WO  WO 2006/106506  10/2006
WO  WO 2006/138552  12/2006
WO  WO2008/093341   8/2008

OTHER PUBLICATIONS

Dosunmu et al., Electrospinning of polymer nanofibres from multiple jets on a porous tubular surface Nanotechnology 17 (2006) 1123-1127.*
WutticharoenmongkolPreparation and Characterization of Novel Bone Scaffolds Based on Electrospun Polycaprolactone Fibers Filled with Nanoparticles Macromol. Biosci. 2006, 6, 70-77.*
Wutticharoenmongkol, et al., Osteoblastic Phenotype Expression of MC3T3-E1 Cultured on Electrospun Polycaprolactone Fiber Mats Filled with Hydroxyapatite Nanoparticles Biomacromolecules 2007, 8, 2602-2610.*
Kim et al Bioactive glass nanofiber—collagen nanocomposite as a novel bone regeneration matrix Jul. 18, 2006 in Wiley InterScience (www.interscience.wiley.com). DOI: 10.1002/jbm.A.30848.*
Huang et al., Journal of Materials Science: Materials in Medicine 16 (2005) 1137-1142 Novel deposition of nano-sized silicon substituted hydroxyapatite by electrostatic spraying.*
Response Dated Jul. 5, 2010 to Communication Pursuant to Article 94(3) EPC of Mar. 5, 2010 From the European Patent Office Re.: Application No. 08702713.2.
International Preliminary Report on Patentability Dated Aug. 4, 2009 From the International Bureau of WIPO Re.: Application No. PCT/IL2008/000134.
International Search Report Dated May 8, 2009 From the International Searching Authority Re.: Application No. PCT/IL2008/000134.
Written Opinion Dated May 8, 2009 From the International Searching Authority Re.: Application No. PCT/IL2008/000134.
Li et al. "Electrospun Silk-BMP-2 Scaffolds for Bone Tissue Engineering", Biomaterials, 27:3115-3124, 2006.
Nie et al. "Fabrication and Characterization of PLGA/HAp Composite Scaffolds for Delivery of BMP-2 Plasmid DNA", Journal of Controlled Release, 120: 111-121, 2007.
Venugopal et al. "Biocomposite Nanofibres and Osteoblasts for Bone Tissue Engineering", Nanotechnology, XP020119794, 18(5): 1-8, Jan. 9, 2007. 'Materials and Methods', 'Results and Discussion'.
Venugopal et al. "Mineralization of Osteoblasts With Electrospun Collagen/Hydroxyapatite Nanofibers", Journal of Materials Science: Materials in Medicine, 8 P., 2007.
Yoshimoto et al. "A Biodegradable Nanofiber Scaffold by Electrospinning and Its Potential for Bone Tissue Engineering", Biomaterials, XP004413511, 24(12): 2077-2082, May 1, 2003.
Communication Pursuant to Article 94(3) EPC Dated Mar. 5, 2010 From the European Patent Office Re.: Application No. 08702713.2.
Communication Pursuant to Article 94(3) EPC Dated Aug. 10, 2011 From the European Patent Office Re. Application No. 08702713.2.
Office Action Dated Jun. 20, 2012 From the Israel Patent Office Re. Application No. 200086 and Its Translation Into English.

* cited by examiner

*Primary Examiner* — Maria Leavitt

(57) ABSTRACT

A porous scaffold is disclosed, the porous scaffold comprising electrospun polymeric nanofibers, wherein an average diameter of a pore of the porous scaffold is about 300 μm is disclosed. An average diameter of the polymeric nanofibers ranges from about 100 to 400 nm. The scaffold may comprise a plurality of particles, the particles being greater than about 1 μm in diameter. Methods of fabricating scaffolds, methods for generating tissue and methods of using scaffolds for tissue reconstruction are also disclosed.

18 Claims, 9 Drawing Sheets
(9 of 9 Drawing Sheet(s) Filed in Color)

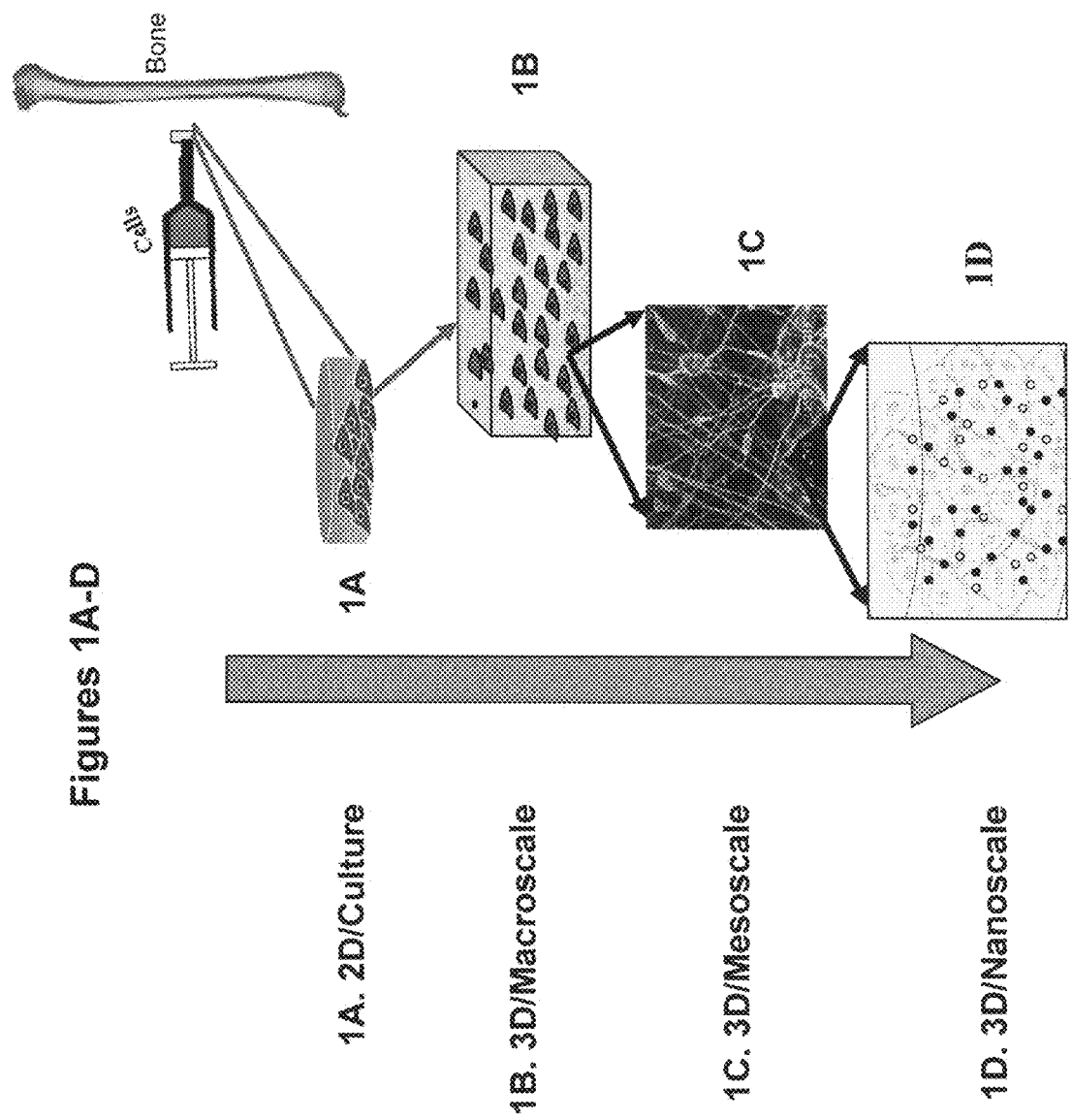

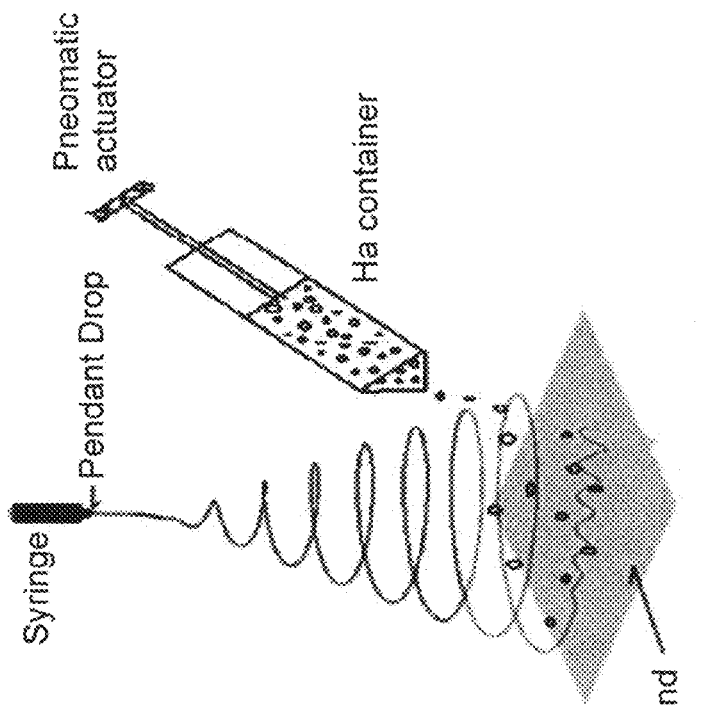
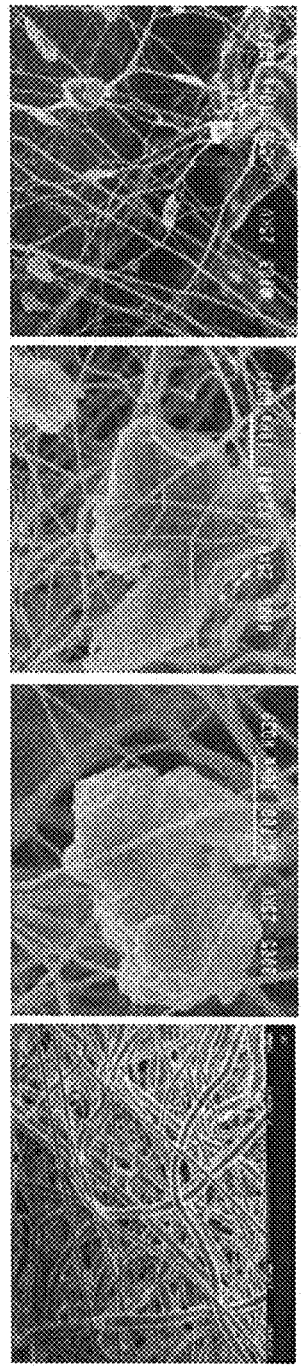
Fig. 2A
Fig. 2B  Fig. 2C  Fig. 2D  Fig. 2E

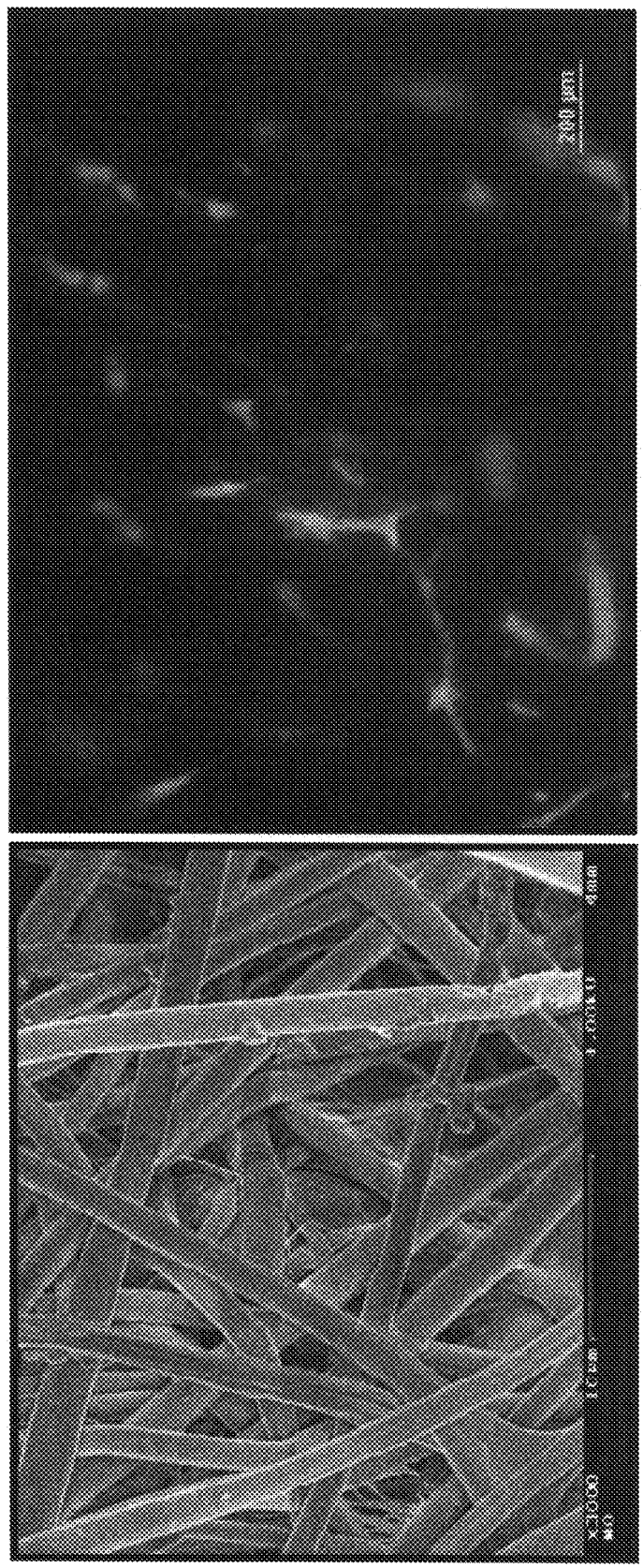
Figures 3A-B

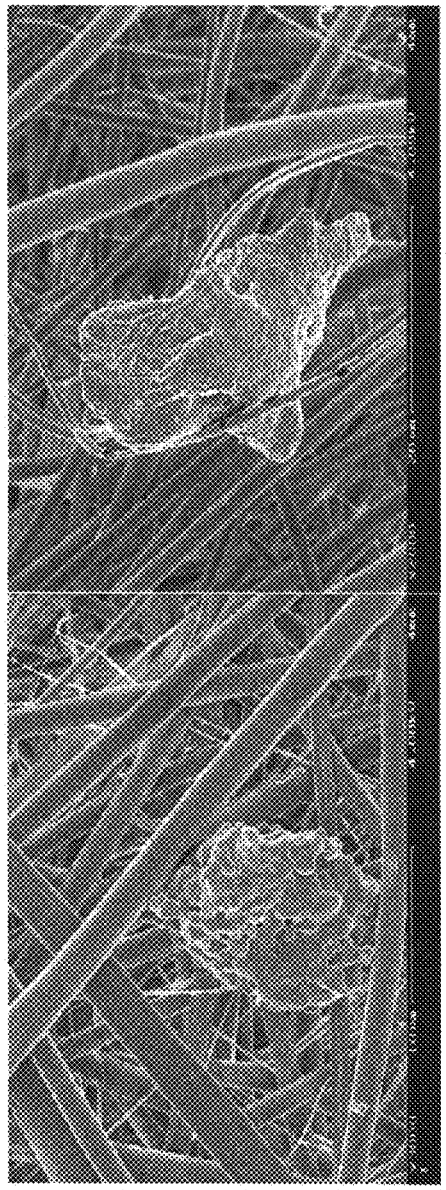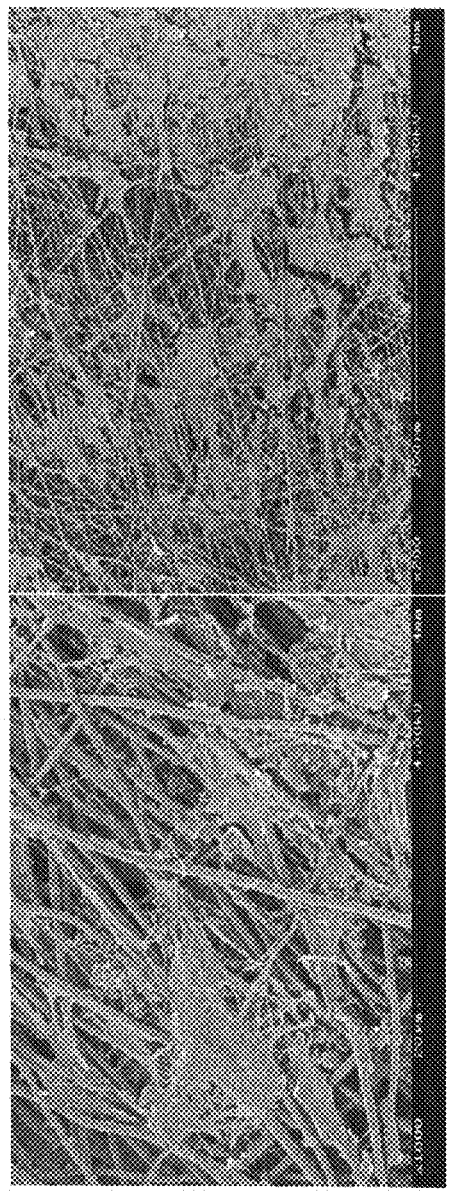
Figures 4A-D

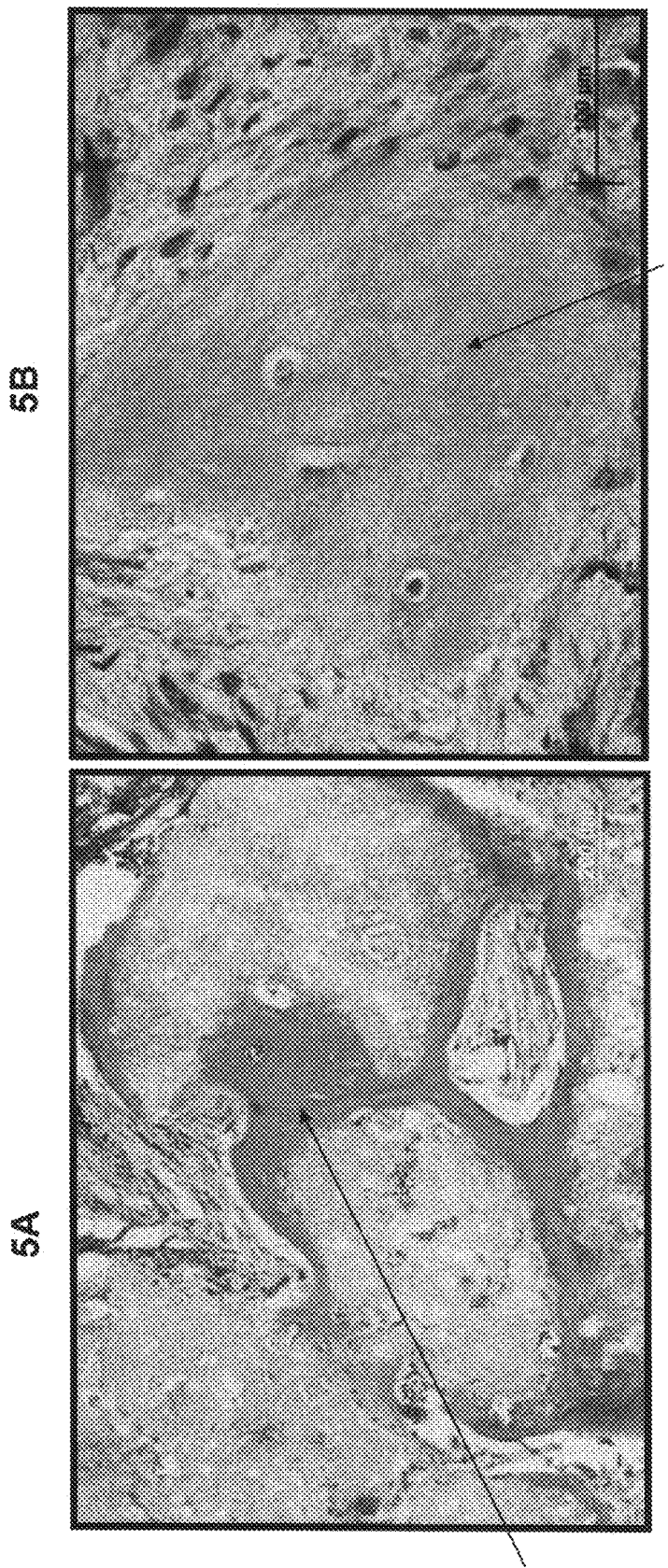
Figures 5A-B

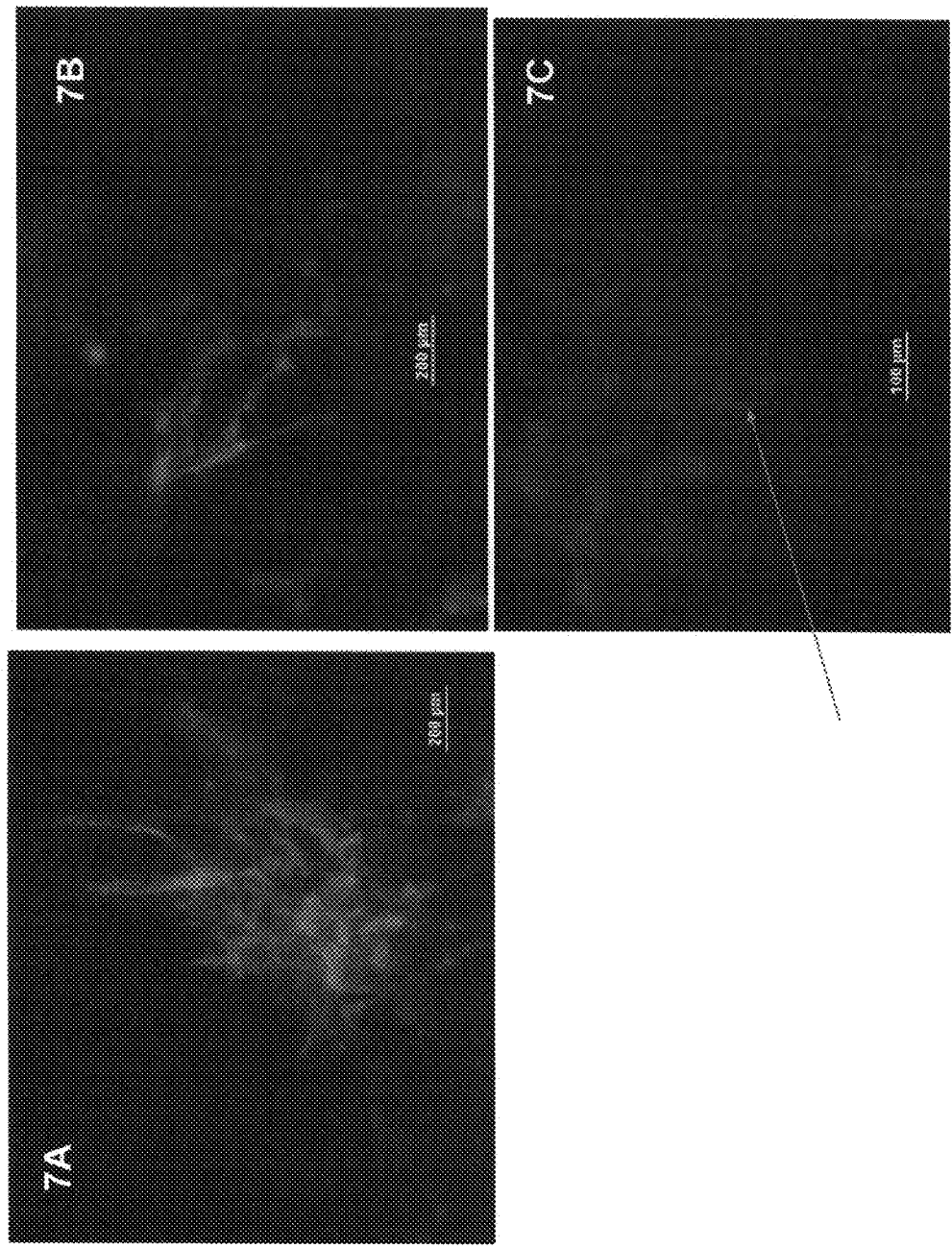
Figures 7A-C

Figures 8A-B
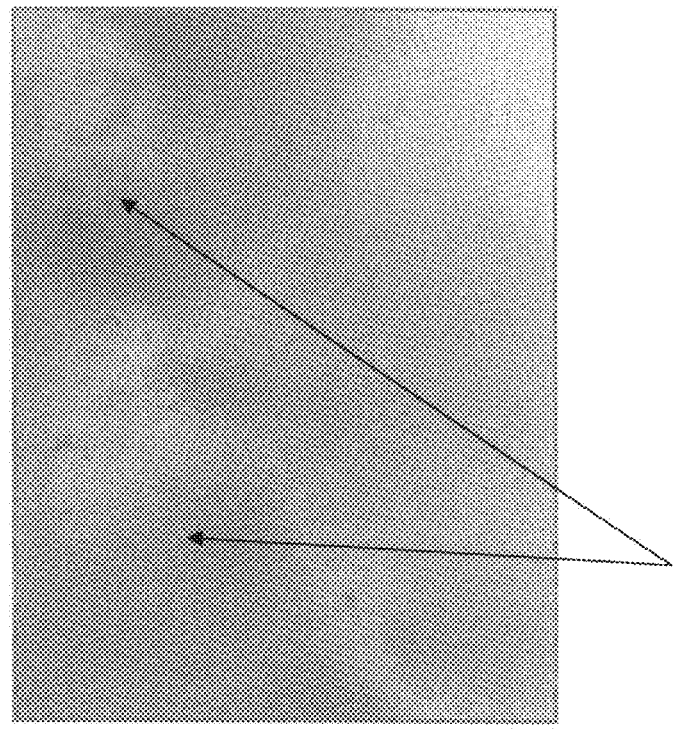

ELECTROSPUN SCAFFOLDS AND METHODS OF GENERATING AND USING SAME

RELATED APPLICATIONS

The application is a National Phase Application of PCT Patent Application No. PCT/IL2008/000134 having International Filing Date of Jan. 31, 2008, which claims benefit under 35 U.S.C. §119(e) from U.S. Provisional Patent Application No. 60/898,394, filed on Jan. 31, 2007. The contents of the above Applications are all incorporated herein by reference.

FIELD AND BACKGROUND OF THE INVENTION

The present invention, in some embodiments thereof, relates to an electrospun scaffold comprising polymeric nanofibers and particles and, more particularly, but not exclusively, to the use of same for bone or connective tissue regeneration.

The need for bone repair is one of the major concerns of regenerative medicine. The key step in the modern approach of bone tissue engineering is the design and fabrication of porous three dimensional (3D) scaffolds. These 3D scaffolds serve as temporary artificial extracellular matrices, accommodating cells and supporting three-dimensional tissue regeneration. In order to achieve these goals, the scaffold's surface chemistry must be suitable for cell attachment and the pore size must allow cellular proliferation. The design of scaffolds that mimic the biological functions of the extracellular matrix, without eliciting an immunological reaction, is a major challenge in tissue engineering and bone repair.

Various applications utilizing scaffolds for tissue engineering and bone repair have been previously described, some are summarized infra.

Hydrogel scaffolds were demonstrated to provide biodegradable 3D structures, which promote cell growth and differentiation. Srouji et al. have demonstrated that these scaffolds promote osteogenic differentiation of bone marrow mesenchymal stem cells (MSCs) [Srouji et al., Microsc Res Tech. (2005) 66(2-3):132-8.]. Hydrogel scaffolds impregnated with growth factors have also been contemplated for treatment of bone defects. For example, bone morphogenetic protein-2 (BMP-2) [Yamamoto et al., J Biomater Sci Polym Ed. (1998) 9(5): 439-58], transforming growth factor beta-1 (TGF-beta1) [Yamamoto et al., J Control Release. (2000) 64(1-3): 133-42] and Insulin-like Growth Factor-1 (IGF-1) [Srouji et al., Cell Tissue Bank. (2004) 5(4):223-30] were all shown to enhance bone regeneration and healing.

PCT Publication No. WO06036826 discloses tissue engineering scaffolds for in vitro and in vivo use (e.g. for drug delivery or for supporting cell attachment and growth). These scaffolds comprise a nanofibrous, nanoporous hydrogel formed from self-assembling peptides. The peptides comprising the hydrogel may be biodegradable materials, include ceramics (e.g. hydroxylapatite), biodegradable polymers, including polycaprolactone (PCL) and polylactic acid (PLA), or non-biodegradable materials (e.g. silk). Furthermore, these scaffolds comprise cells (e.g. stem cells, progenitor cells).

U.S. Pat. No. 7,122,057 discloses use of engineered regenerative biostructures (ERB) as a bone substitute. These biostructures comprise ceramic materials (e.g. hydroxylapatite) that are partially joined to each other in a manner that leaves some porosity therebetween. According to U.S. Pat. No. 7,122,057, the micro- and meso-architecture of the ERBs is designed to be consistent and defined. Furthermore, the ERBs may comprise cells (e.g. MSCs) or polymers (e.g. PLA and PCL).

Another approach for designing 3D porous scaffolds for use in tissue engineering is electrospinning. Electrospinning is a process that uses an electric field to control the formation and deposition of polymers. This process is remarkably efficient, rapid, and inexpensive. In electrospinning, a polymer solution or melt is injected with an electrical potential to create a charge imbalance and placed in proximity to a grounded target. At a critical voltage, the charge imbalance begins to overcome the surface tension of the polymer source, forming an electrically charged jet. The jet within the electric charge is directed toward the grounded target, during which time the solvent evaporates and fibers are formed. Electrospinning produces a single continuous nanofibrous filament that collects on the grounded target as a non-woven fabric.

Electrospinning yields scaffolds with a high porosity. The nanometer to micrometer fibers comprised therein combine in non-woven networks resembling the natural extracellular matrix. Because a collector is used that has the desired shape of the scaffold, complex scaffold geometries can be utilized. Moreover, in the electrospinning process, many parameters can be altered to optimize the properties of the final product.

Many different polymers have been previously contemplated in electrospinning; these include several classes of biomaterials such as synthetic polymers (organic and inorganic), ceramics and native polymers. Furthermore, the polymers can be biodegradable or non-degradable.

PCL scaffolds, produced by electrospinning, were reported to provide biocompatible structures for osteogenesis [Yoshimoto et al., Biomaterials (2003) 24: 2077-2082] and for chondrogenesis [Li et al, Biomaterials (2005) 26: 599-609]. Other synthetic polymers, such as polyglycolic acid (PGA) and poly(Lactide-co-Glycolide) (PLGA), and natural macromolecules, such as collagen and fibrinogen, have been processed into fibrous non-woven scaffolds for tissue engineering research [Li et al., J Biomed Mater Res. (2002) 60(4): 613-21; Yoshimoto et al., Biomaterials. (2003) 24(12):2077-82].

Electrospun scaffolds fabricated from both synthetic polymers (such as polycaprolactone (PCL) and poly (lactide-co-glycolide; PLGA)) and natural polymers (such as silk and collagen) containing nanoparticles of calcium carbonate (CaCO3) or hydroxylapatite (HA) have been successfully used as bone scaffolding materials—see for example [Wutticharoenmongkol P. et al., J Nanosci Nanotechnol. (2006) 6(2):514-22; Li et al., Biomaterials (2006) 27:3115-3124; Venugopal et al., J Mater Sci: Mater Med (2007) Epub; Nie and Wang, J Controlled Release (2007) 120:111-121 and U.S. Publication No. 20050112349].

SUMMARY OF THE INVENTION

According to an aspect of some embodiments of the present invention there is provided a scaffold comprising electrospun polymeric nanofibers, the scaffold being a porous scaffold, wherein an average diameter of a pore of the porous scaffold is about 300 µm.

According to an aspect of some embodiments of the present invention there is provided a scaffold comprising electrospun polymeric nanofibers and a plurality of particles, wherein an average diameter of the polymeric nanofibers ranges from about 100 to 400 nm and whereas the particles are greater than about 1 µm in diameter.

According to an aspect of some embodiments of the present invention there is provided a method of fabricating a scaffold comprising dispensing within an electrostatic field from a first dispenser at least one liquefied polymer into a collector, and concomitantly dispensing from a second dispenser a dispersion of particles into the collector, thereby fabricating a scaffold.

According to an aspect of some embodiments of the present invention there is provided a method of fabricating a scaffold comprising collecting an electrospun polymer in a collector, and concomitantly dispensing particles into the collector, the particles being greater than about 1 μm in diameter, thereby fabricating a scaffold.

According to an aspect of some embodiments of the present invention there is provided a scaffold generated according to the method of the present invention.

According to an aspect of some embodiments of the present invention there is provided a method of generating a tissue, the method comprising seeding cells on the scaffolds of the present invention, thereby generating the tissue.

According to an aspect of some embodiments of the present invention there is provided use of a porous scaffold for tissue reconstruction, wherein the scaffold comprises electrospun polymeric nanofibers and wherein an average diameter of a pore of the porous scaffold is about 300 μm.

According to an aspect of some embodiments of the present invention there is provided use of a scaffold for tissue reconstruction, wherein the scaffold comprises electrospun polymeric nanofibers and a plurality of particles, wherein an average diameter of the polymeric nanofibers range from about 100 to 400 nm and the particles are greater than about 1 μm in diameter.

According to an aspect of some embodiments of the present invention there is provided a method of regenerating a tissue in a subject in need thereof the method comprising implanting the scaffolds of the present invention in a damaged tissue region of the subject, thereby regenerating the tissue.

According to some embodiments of the invention, the polymeric nanofibers comprise biodegradable polymers.

According to some embodiments of the invention, the biodegradable polymers are selected from the group consisting of polycaprolactone (PCL), polylactic acid (PLA), polyglycolic acid (PGA), and poly(Lactide-co-Glycolide) (PLGA).

According to some embodiments of the invention, the polymeric nanofibers comprise non-biodegradable polymers.

According to some embodiments of the invention, the polymeric nanofibers comprise biodegradable polymers and non-biodegradable polymers.

According to some embodiments of the invention, an average diameter of the polymeric nanofibers ranges from about 100 to 400 nm.

According to some embodiments of the invention, the scaffold further comprises a plurality of particles.

According to some embodiments of the invention, the plurality of particles is embedded between the polymeric nanofibers.

According to some embodiments of the invention, the plurality of particles are osteoconductive particles.

According to some embodiments of the invention, the particles are selected from the group consisting of hydroxylapatite (HA), calcium titanate and tricalcium phosphate (TCP).

According to some embodiments of the invention, the particles comprise hydroxylapatite (HA).

According to some embodiments of the invention, the particles are greater than about 1 μm in diameter.

According to some embodiments of the invention, the scaffold further comprises a plurality of cells seeded on or within the scaffold.

According to some embodiments of the invention, the plurality of cells is a heterogeneous population of cells.

According to some embodiments of the invention, the plurality of cells is a homogeneous population of cells.

According to some embodiments of the invention, the cells are progenitor bone cells.

According to some embodiments of the invention, the cells are stem cells.

According to some embodiments of the invention, the stem cells are mesenchymal stem cells.

According to some embodiments of the invention, the cells are selected from the group consisting connective tissue cells, chondrocytes and osteoblasts.

According to some embodiments of the invention, the scaffold is a non-woven scaffold.

According to some embodiments of the invention, a volume of the scaffold is greater than about 1 $mm^3$.

According to some embodiments of the invention, the scaffold further comprises at least one agent for promoting cell adhesion, colonization, proliferation, differentiation, extravasation and/or migration.

According to some embodiments of the invention, a volume of the polymeric nanofibers is less than about 10% of a volume of the scaffold.

According to some embodiments of the invention, the scaffold is a porous scaffold.

According to some embodiments of the invention, a pore of the porous scaffold comprises an average pore diameter of about 300 μm.

According to some embodiments of the invention, the method further comprising dispensing within the electrostatic field an adhesive agent from a third dispenser into the collector, wherein the dispensing is effected concomitantly with the dispensing from the first dispenser of the at least one liquefied polymer.

According to some embodiments of the invention, the adhesive agent is selected from the group consisting of gelatin, fibrin, fibronectin, collagen, and RGD.

According to some embodiments of the invention, the liquefied polymer comprises a biodegradable polymer.

According to some embodiments of the invention, the biodegradable polymer is selected from the group consisting of polycaprolactone (PCL), polylactic acid (PLA), polyglycolic acid (PGA), and poly(Lactide-co-Glycolide) (PLGA).

According to some embodiments of the invention, the liquefied polymer comprises a non-biodegradable polymer.

According to some embodiments of the invention, the liquefied polymer comprises a biodegradable polymer and a non-biodegradable polymer.

According to some embodiments of the invention, the cells comprise bone cells.

According to some embodiments of the invention, the cells comprise cartilage cells.

According to some embodiments of the invention, the tissue comprises connective tissue.

According to some embodiments of the invention, the method further comprises implanting the tissue into a subject.

According to some embodiments of the invention, the scaffold comprises cells.

According to some embodiments of the invention, the subject has a pathology characterized by bone or cartilage damage or loss.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D illustrate a schematic illustration of the levels of hierarchy of 3D scaffold organization and design. FIG. 1A depicts bone marrow cell aspirates cultured in a 2D culture plate; FIG. 1B depicts transfer of cells to a 3D macroscale scaffold to increase cell-scaffold interactions; FIG. 1C depicts a 3D electrospun nanofibrous porous scaffold containing HA particles designed to mimic the natural mesoscale 3D environment of the bone (of note, this scaffold provides the volume needed for the cells); and FIG. 1D depicts a biomimetic bioactive electrospun scaffold containing signaling molecules (e.g. growth factors) and HA particles. Of note, this scaffold mimics the natural cell/scaffold interactions at the nanoscale level.

Figure 1E:
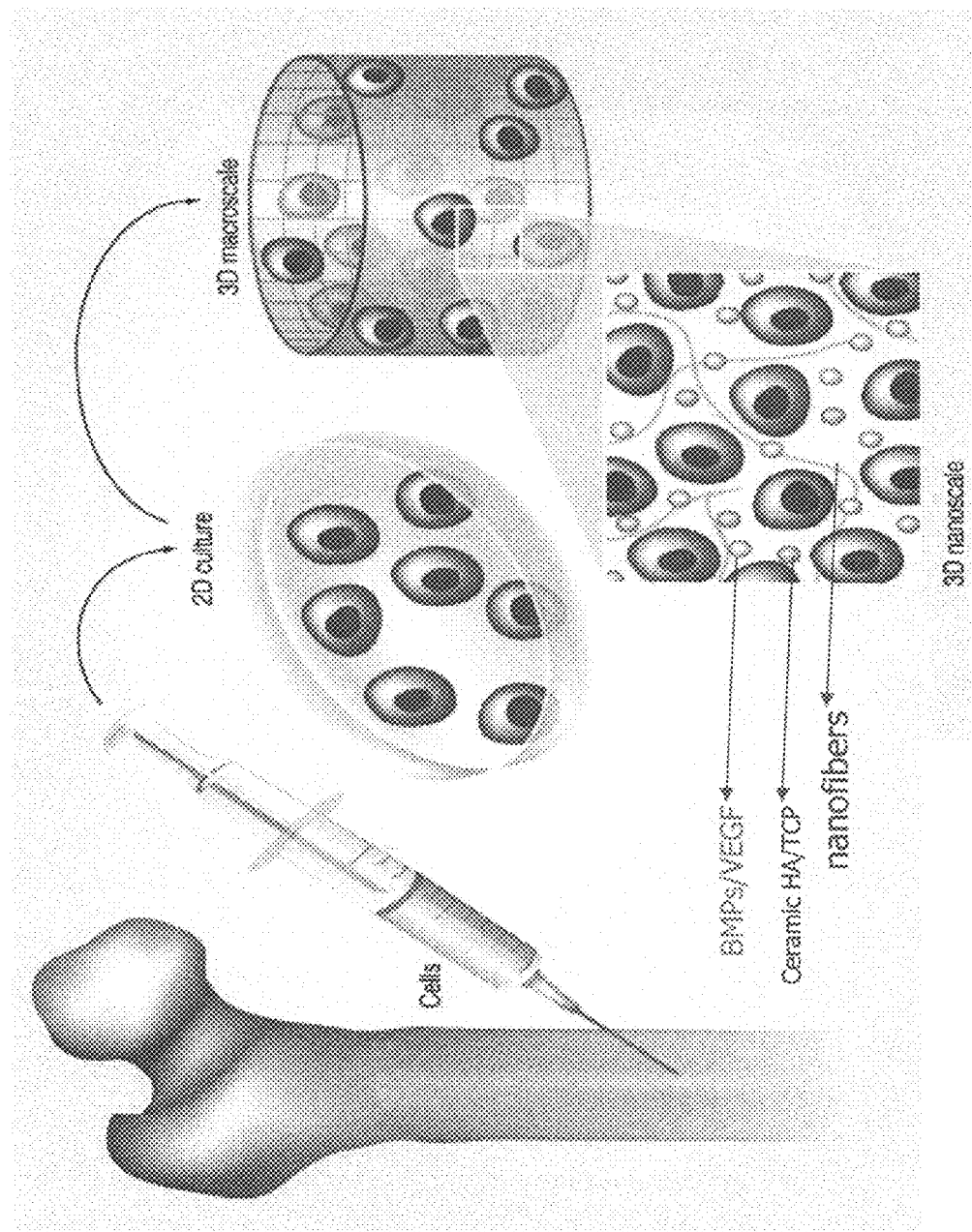

FIG. 1E illustrate a schematic illustration of 3D scaffold for bone repair. The illustration points out the nanofibers, the particles (e.g. HA/TCP) and signaling molecules (e.g. growth factors).

FIGS. 2A-E illustrate a scanning electron micrograph (SEM) of newly designed electrospun composite scaffold. FIG. 2B depicts electrospun PCL nanofibers; FIGS. 2C-E depict electrospun PCL nanofibers with HA particles. FIG. 2C×3,700; FIG. 2D×2,000; FIG. 2E×550. Of note, this electrospun scaffold contains HA particles providing a highly porous scaffold with increased volume.

FIGS. 3A-B are images of PCL/Gelatin/HA scaffolds seeded with GFP-labeled cells. FIG. 3A shows the electrospun scaffold as imaged using a scanning electron microscope (SEM), showing a porous fibrous structure; and FIG. 3B shows the scaffold cultured with GFP-labeled osteoprogenitor cells, as imaged using a fluorescent microscope. Of note, the cells are spread along the fibers.

FIGS. 4A-D are images of the electrospun scaffolds. FIGS. 4A-B show pre-seeded PCL/Gelatin/HA scaffolds (SEM images); and FIG. 4C-D show SEM images of the scaffolds together with osteoprogenitor cells.

FIGS. 5A-B are images of in vivo ectopic (subcutaneous) bone formation following implantation of electrospun PCL/Gelatin/HA scaffolds. Cells and fibers were stained with Masson's Trichrome stain Subcutaneous new bone formation is shown by arrows.

Figure 6:
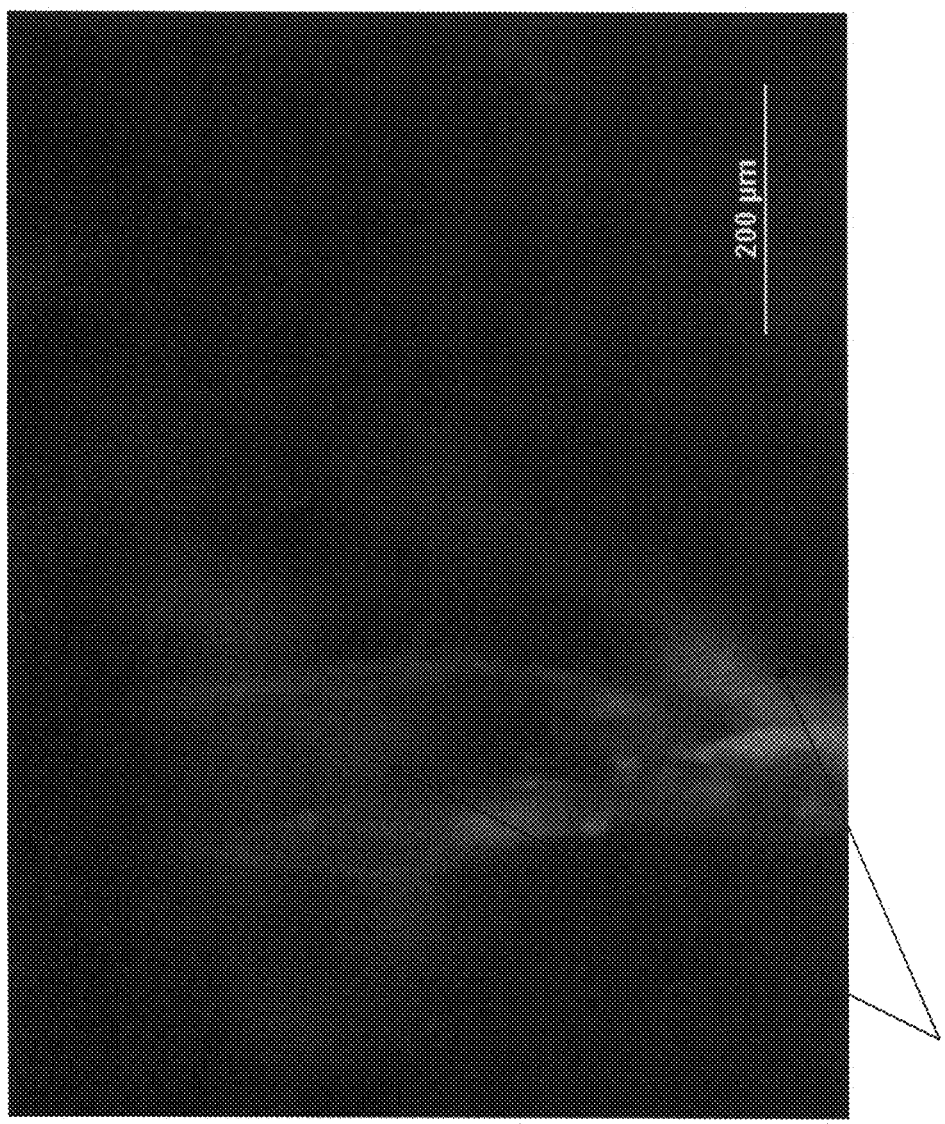

FIG. 6 is a image of an electrospun PCL/Gelatin/HA scaffold with GFP-labeled cells, as imaged using a fluorescent microscope. Note electrospun fibers between the cells (shown by arrows).

FIGS. 7A-C are images of GFP-labeled cells cultured (1 week) on PCL/Gelatin/HA electrospun scaffolds.

FIGS. 8A-B are images of light microscopy images of the scaffolds. FIG. 8A shows light microscopy view of the cell seeded-scaffold with the mineral particles (dark shadows, shown by arrows); and FIG. 8B shows fluorescent view of GFP-labeled cells seeded in the scaffold with the mineral particles (cells are green fluorescent).

DESCRIPTION OF SPECIFIC EMBODIMENTS OF THE INVENTION

The present invention, in some embodiments thereof, relates to electrospun scaffolds comprising polymeric nanofibers and particles and to the use of same for tissue regeneration.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Bone repair is one of the major concerns of regenerative medicine. The modern approach to bone tissue engineering is the design and fabrication of porous three dimensional (3D) scaffolds which serve as temporary artificial extracellular matrices, accommodating cells and supporting 3D tissue regeneration. Various scaffolds for tissue engineering, which support cell growth and differentiation, have been previously described. These include hydrogel scaffolds and electrospun scaffolds (explained in detail in the field and background section hereinabove).

While reducing some embodiments of the present invention to practice, the present inventors have generated electrospun scaffolds comprising polymeric nanofibers in between which are situated particles greater than 1 μm in diameter, which overall increases the scaffold volume by rendering it highly porous with an average pore size of 300 μm. Such scaffolds are particularly suitable for tissue growth since they allow the penetration of cells. PCL/Gelatin/HA Electrospun scaffolds generated according to the present teachings were shown to support in vitro osteogenic cell proliferation (FIGS. 6, 7A-C and 8A-B). In addition, as is further shown in FIGS. 5A-B, implantation of such scaffolds comprising osteoprogenitor cells into nude mice induced bone formation as early as 8 weeks following the time of implantation.

Accordingly, these scaffolds may serve as powerful tools in the field of tissue regeneration.

Thus, according to one aspect of the present invention there is provided a method of fabricating a scaffold comprising collecting an electrospun polymer in a collector, and concomitantly dispensing particles into the collector, the particles being greater than about 1 μm in diameter, thereby fabricating a scaffold.

As used herein, the term "scaffold" refers to a 3D matrix upon which cells may be cultured (i.e., survive and preferably proliferate for a predetermined time period).

As used herein, the phrase "fabricating a scaffold" refers to the process of generating or manufacturing a scaffold. According to this aspect, the fabricating is effected by an electrospinning process.

As used herein, the term "electrospinning" refers to a technology which produces electrospun fibers (e.g. nanofibers) from a polymer solution. During this process, one or more polymers are liquefied (i.e. melted or dissolved) and placed in a dispenser. An electrostatic field is employed to generate a positively charged jet from the dispenser to the collector. Thus, a dispenser (e.g., a syringe with metallic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Reverse polarity for establishing motions of a negatively charged jet from the dispenser to the collector is also contemplated. At the critical voltage, the charge repulsion begins to overcome the surface tension of the liquid drop. The charged jets depart from the dispenser and travel within the electrostatic field towards the collector. Moving with high velocity in the inter-electrode space, the jet stretches and the solvent therein evaporates, thus forming fibers which are collected on the collector forming the electrospun scaffold.

Several parameters may affect the diameter of the fiber, these include, the size of the dispensing hole of the dispenser, the dispensing rate, the strength of the electrostatic field, the distance between the dispenser and/or the concentration of the polymer used for fabricating the electrospun fiber.

The dispenser can be, for example, a syringe with a metal needle or a bath provided with one or more capillary apertures from which the liquefied polymer(s) can be extruded, e.g., under the action of hydrostatic pressure, mechanical pressure, air pressure and high voltage.

According to one embodiment, the collector is a rotating collector which serves for collecting the electrospun scaffold thereupon. Employing a rotating collector can result in an electrospun scaffold with a continuous gradient of porosity. Such a porosity gradient can be achieved by continuous variation in the velocity of the collector or by a longitudinal motion of the dispenser, as disclosed for example in WO06106506, these result in a substantial variation in the density and/or spatial distribution of the fibers on the collector and thus, result in a porosity gradient along the radial direction or along the longitudinal direction of the collector, respectively. Typically, but not obligatorily, the rotating collector has a cylindrical shape (e.g., a drum), however, it will be appreciated that the rotating collector can be also of a planar geometry.

According to another embodiment, the collector is a flat ground collector which serves for collecting the electrospun scaffold thereupon. Employing a flat ground collector enables collection of random nanofibers. It will be appreciated that the flat ground collector is typically a horizontal collector or a vertical collector.

The polymer used to fabricate the scaffolds of the present invention can be natural, synthetic, biocompatible, biodegradable and/or non-biodegradable polymers.

The phrase "synthetic polymer" refers to polymers that are not found in nature, to even if the polymers are made from naturally occurring biomaterials. Examples include, but are not limited to, aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use according to the teachings of the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid and alginate.

The phrase "biocompatible polymer" refers to any polymer (synthetic or natural) which when in contact with cells, tissues or body fluid of an organism does not induce adverse effects such as immunological reactions and/or rejections and the like. It will be appreciated that a biocompatible polymer can also be a biodegradable polymer.

The phrase "biodegradable polymer" refers to a synthetic or natural polymer which can be degraded (i.e., broken down) in the physiological environment such as by proteases. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. Examples of biodegradable polymers include, but are not limited to, collagen (e.g., Collagen I or IV), fibrin, hyaluronic acid, polylactic acid (PLA), polyglycolic acid (PGA), polycaprolactone (PCL), poly(Lactide-co-Glycolide) (PLGA), polydioxanone (PDO), trimethylene carbonate (TMC), polyethyleneglycol (PEG), Collagen, PEG-DMA, Alginate, chitosan copolymers or mixtures thereof.

The phrase "non-biodegradable polymer" refers to a synthetic or natural polymer which is not degraded (i.e., broken down) in the physiological environment. Examples of non-biodegradable polymers include, but are not limited to, nylon, silicon, silk, polyurethane, polycarbonate, polyacrylonitrile, polyethyleneoxide, polyaniline, polyvinyl carbazole, polyvinyl chloride, polyvinyl fluoride, polyvinyl imidazole, polyvinyl alcohol, polystyrene and poly(vinyl phenol), aliphatic polyesters, polyacrylates, polymethacrylate, acyl-substituted cellulose acetates, non-biodegradable polyurethanes, polystyrenes, chlorosulphonated polyolifins, polyethylene oxide, polytetrafluoroethylene, and shape-memory materials such as poly (styrene-block-butadiene), copolymers or mixtures thereof.

It will be appreciated that more than one polymer may be used to fabricate the scaffolds of the present invention. For example, the scaffold may be fabricated from a co-polymer.

The term "co-polymer" as used herein, refers to a polymer of at least two chemically distinct monomers. Non-limiting examples of co-polymers which may be used to fabricate the scaffolds of the present invention include, PLA-PEG, PEGT-PBT, PLA-PGA, PEG-PCL and PCL-PLA.

According to another embodiment of the present invention, the electrospun polymer comprises a mixture of a polymer and a co-polymer, such as biodegradable and non-biodegradable polymers.

As mentioned, the scaffolds of the present invention are fabricated with particles as well as with electrospun polymers.

According to this aspect of the present invention, the particles are dispensed concomitantly with the dispensing of the electrospun polymers, although from a separate dispenser e.g. by air pressure from a pneumatic activator.

It will be appreciated that the concomitant dispensing of the particles from a separate dispenser results in particles being situated between the polymeric fibers and not embedded within the fibers.

As used herein, the term "particles" refers to any finely divided solid non-cellular matter, including powders, filings, crystals, beads and the like, which are capable of being integrated into a scaffold, but without interfering with the scaffolds capability to support cells.

According to one embodiment, the particles are osteoconductive i.e. capable of supporting the growth of bone cells.

Examples of particles which can be used according to the teachings of the present invention include, but are not limited to, calcium titanate, hydroxylapatite (HA), tricalcium phosphate (TCP) and other calcium phosphates and calcium-phosphorus compounds, hydroxylapatite calcium salts, inorganic bone, dental tooth enamel, aragonite, calcite, nacre, graphite, pyrolytic carbon, bioglass, bioceramic, and mixtures thereof.

According to an exemplary embodiment, the particles of the present invention are greater than about 0.5 µm in diameter, greater than about 1 µm in diameter, greater than about 1.5 µm in diameter, greater than about 2 µm in diameter, greater than about 2.5 µm in diameter, greater than about 3 µm in diameter, greater than about 3.5 µm in diameter, greater than about 4 µm in diameter, greater than about 4.5 µm in diameter, greater than about 5 µm in diameter, greater than about 5.5 µm in diameter, greater than about 6 µm in diameter, greater than about 6.5 µm in diameter, greater than about 7 µm in diameter, greater than about 7.5 µm in diameter, or greater than about 8 µm in diameter.

According to another exemplary embodiment, adhesive agents are included in the scaffolds of the present invention. Such adhesive agents may be used to unite or bond the electrospun polymers together.

Thus, according to another embodiment of the present invention, the method further comprises dispensing an adhesive agent into the collector. Dispensing may be effected in a single composition with the polymer or in a separate dispenser (i.e. from the second or third dispenser). When the adhesive agent is dispensed from the second or third dispenser, it is effected concomitantly with dispensing of the first dispenser (i.e., polymer) within the electrostatic field. Such an adhesive agent may include, without being limited to, gelatin, fibrin, fibronectin, collagen or RGB. Ratios of adhesive agents (e.g. gelatin): polymer may be about 50:50, may be about 40:60, may be about 30:70, may be about 20:80, or may be about 10:90.

Implementation of the methods of the present invention result in the generation of scaffolds suitable for aiding in the process of tissue regeneration.

Thus, according to another aspect of the present invention there is provided a scaffold comprising electrospun polymeric nanofibers and a plurality of particles, wherein an average diameter of the polymeric nanofibers ranges from about 100 to 400 nm and whereas the particles are greater than about 1 µm in diameter.

It will be appreciated that, the scaffolds of the present invention may comprise a single type of particles or alternatively may comprise two or more types of particles. Examples of particles which can be used according to the teachings of the present invention are further detailed hereinabove.

As used herein, the phrase "polymeric nanofibers" refers to polymer fibers having diameters typically between 10 nm and 1000 nm. Exemplary sub-ranges contemplated by the present invention include between 100 and 1000 nm between 100 and 800 nm, between 100 and 600 nm, and between 100 and 400 nm. Other exemplary ranges include 10-100 nm, 10-200 nm and 10-500 nm. As mentioned, the polymeric nanofibers of the scaffolds of the present invention are preferably generated by an electrospinning processes.

When the electrospun scaffold is made of a single fiber (e.g. nanofiber), the fiber is folded thereupon, hence can be viewed as a plurality of connected fibers. It is to be understood that a more detailed reference to a plurality of fibers is not intended to limit the scope of the present invention to such particular case. Thus, unless otherwise defined, any reference herein to a "plurality of fibers" applies also to a single fiber and vice versa.

The polymeric nanofibers of the electrospun scaffold can be arranged in a single layer, but, more preferably, the nanofibers define a plurality of layers hence forming a 3D structure. The polymeric nanofibers can have a general random orientation, or a preferred orientation, as desired e.g., when the nanofibers are collected on a cylindrical collector such as a drum, the polymeric nanofibers can be aligned predominantly axially or predominantly circumferentially. Different layers of the electrospun scaffold can have different orientation characteristics. For example, without limiting the scope of the present invention to any specific ordering or number of layers, the nanofibers of a first layer can have a first predominant orientation, the nanofibers of a second layer can have a second predominant orientation, and the nanofibers of third layer can have general random orientation.

It will be appreciated that changes in the fiber diameter may affect the average fiber weight-per-volume of the electrospun scaffold. Fiber weight-per-volume of the electrospun scaffold can also be affected by using more than one syringe alternatively or together with variable polymer concentrations in each syringe.

Thus, according to an embodiment of this aspect of the invention, an amount of polymeric nanofibers per 1 mm$^3$ scaffold is less than about 0.1 mm$^3$ (10% of the volume).

Typically, the scaffolds of the present invention comprise at least 1 particle per 10 polymeric nanofibers (i.e. a ratio of particle volume:polymer volume is typically greater than 1:10). Thus the particles comprise at least 1% of the scaffold volume.

Weight-per-volume of the electrospun scaffold is also effected by the particle size. It will be appreciated that fabricating scaffolds using large particles may result in a larger scaffold volume.

Since, the particles used in the scaffolds of the present invention are large (about 1 µm in diameter), the scaffolds typically comprise a large volume. According to the teachings of the present invention, the volume of the scaffold may be greater than about 1 mm$^3$, greater than about 2 mm$^3$, greater than about 3 mm$^3$, greater than about 4 mm$^3$, greater than about 5 mm$^3$, or greater than about 6 mm$^3$.

Furthermore, it will be appreciated that using large particles within the scaffolds of the present invention leads to the generation of large pores within the electrospun scaffold.

Accordingly, the scaffolds used in the present invention may comprise pores having an average diameter of about 200 µm, of about 250 of about 300 µm, of about 350 or about 400 µm.

It will be appreciated that the scaffolds of the present invention may comprise a porosity gradient (e.g. a continuous or step-wise gradient).

Scaffolds may be in the form of solid-cast structures, open-pore foams, woven, knitted constructs, or in the form of a non-woven scaffold. Furthermore, the electrospun scaffolds may comprise any shape including, without limitation, a round shape or a cube shape.

Therapeutic compounds or agents that modify cellular activity can also be incorporated (e.g. attached to, coated on, embedded or impregnated) into the scaffold material. In addition, agents that act to increase cell attachment, cell spreading, cell proliferation, cell differentiation and/or cell migration in the scaffold may also be incorporated into the scaffold. Such agents can be biological agents such as an amino acid, peptides, polypeptides, proteins, DNA, RNA, lipids and/or proteoglycans.

Suitable proteins which can be used along with the present invention include, but are not limited to, extracellular matrix proteins [e.g., fibrinogen, collagen, fibronectin, vimentin, microtubule-associated protein 1 D, Neurite outgrowth factor (NOF), bacterial cellulose (BC), laminin and gelatin], cell adhesion proteins [e.g., integrin, proteoglycan, glycosaminoglycan, laminin, intercellular adhesion molecule (ICAM) 1, N-CAM, cadherin, tenascin, gicerin, RGD peptide and nerve injury induced protein 2 (ninjurin2)], growth factors [epidermal growth factor, transforming growth factor-α, fibroblast growth factor-acidic, bone morphogenic protein, fibroblast growth factor-basic, erythropoietin, thrombopoietin, hepatocyte growth factor, insulin-like growth factor-I, insulin-like growth factor-II, Interferon-β, platelet-derived growth factor, Vascular Endothelial Growth Factor and angiopeptin], cytokines [e.g., M-CSF, IL-1 beta, IL-8, beta-thromboglobulin, EMAP-II, G-CSF and IL-10], proteases [pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2] and protease substrates.

Additionally and/or alternatively, the scaffolds of the present invention may comprise an antiproliferative agent (e.g., rapamycin, paclitaxel, tranilast, Atorvastatin and trapidil), an immunosuppressant drug (e.g., sirolimus, tacrolimus and Cyclosporine) and/or a non-thrombogenic or anti-adhesive substance (e.g., tissue plasminogen activator, reteplase, TNK-tPA, glycoprotein IIb/IIIa inhibitors, clopidogrel, aspirin, heparin and low molecular weight heparins such as enoxiparin and dalteparin).

The compounds and/or agents can be attached to at least a portion of the scaffold. Such attachments can be performed using e.g., cross-linking (chemical or light mediated) of the agent with the polymer solution or the electrospun fiber formed therefrom (e.g., PLC and the agent). Additionally or alternatively, the agent can be embedded in electrospun nanofibers having the core-shell structure essentially as described in Sun et al. (e.g., see Sun et al., "Compound Core/shell Polymer Nanofibers by Co-Electrospinning", *Advanced Materials,* 15, 22:1929-1936, 2003). Still additionally or alternatively the agents can be impregnated in the electrospun scaffold by soaking the electrospun scaffold or at least a portion of the polymer fibers forming the electrospun scaffold in a solution containing such an agent.

Following generation, the scaffolds of the present invention are typically sterilized, for example by oxygen plasma, following which they are seeded with cells.

As used herein, the term "seeding" refers to plating, placing and/or dropping the cells of the present invention into the electrospun scaffold of the present invention. It will be appreciated that the concentration of cells which are seeded on or within the electrospun scaffold depends on the type of cells used and the composition of the electrospun scaffold.

Techniques for seeding cells onto or into a scaffold are well known in the art, and include, without being limited to, static seeding, filtration seeding and centrifugation seeding. Static seeding includes incubation of a cell-medium suspension in the presence of the scaffold under static conditions and results in non-uniformity cell distribution (depending on the volume of the cell suspension); filtration seeding results in a more uniform cell distribution; and centrifugation seeding is an efficient and brief seeding method (see for example EP 19980203774).

The cells may be seeded directly onto the scaffold, or alternatively, the cells may be mixed with a gel which is then absorbed onto the interior and exterior surfaces of the scaffold and which may fill some of the pores of the scaffold. Capillary forces will retain the gel on the scaffold before hardening, or the gel may be allowed to harden on the scaffold to become more self-supporting. Alternatively, the cells may be combined with a cell support substrate in the form of a gel optionally including extracellular matrix components.

The cells may comprise a heterogeneous population of cells or alternatively the cells may comprise a homogeneous population of cells. Such cells can be for example, stem cells (such as embryonic stem cells, bone marrow stem cells, cord blood cells, mesenchymal stem cells, adult tissue stem cells), progenitor cells (e.g. progenitor bone cells), or differentiated cells such as chondrocytes, osteoblasts, connective tissue cells (e.g., fibrocytes, fibroblasts and adipose cells), endothelial and epithelial cells. Furthermore, the cells may be of autologous origin or non-autologous origin, such as postpartum-derived cells (as described in U.S. application Ser. Nos. 10/887,012 and 10/887,446). Typically the cells are selected according to the tissue being generated.

According to an embodiment of this aspect of the present invention, the cells are bone or cartilage cells. Non limiting examples of bone and cartilage cells include osteoprogenitor cells, osteoblasts, osteocytes, osteoclasts, and chondrocytes.

As used herein, the phrase "stem cell" refers to cells which are capable of differentiating into other cell types having a particular, specialized function (i.e., "fully differentiated" cells) or remaining in an undifferentiated state hereinafter "pluripotent stem cells".

Following seeding, the scaffolds are routinely examined using a microscope (e.g., an inverted microscope, an axioplan light microscope or an electronic microscope) for evaluation of cell growth, spreading and tissue formation (see for example Examples 1-2).

It will be appreciated that to support cell growth, the cells are seeded in the scaffold in the presence of a culture medium.

The culture medium used by the present invention can be any liquid medium which allows at least cell survival. Such a culture medium can include, for example, salts, sugars, amino acids and minerals in the appropriate concentrations and with various additives and those of skills in the art are capable of determining a suitable culture medium to specific cell types. Non-limiting examples of such culture medium include, phosphate buffered saline, DMEM, MEM, RPMI 1640, McCoy's 5A medium, medium 199 and IMDM (available e.g., from Biological Industries, Beth Ha'emek, Israel; Gibco-Invitrogen Corporation products, Grand Island, N.Y., USA).

The culture medium may be supplemented with various antibiotics (e.g., Penicillin and Streptomycin), growth factors or hormones, specific amino acids (e.g., L-glutamin) cytokines and the like.

For example, as is shown in Example 1 of the Examples section which follows, a culture medium which includes osteogenic supplements (e.g. dexamethasone) is capable of inducing proliferation and differentiation of bone marrow derived mesenchymal stem cells (MSCs) into osteoblasts.

As mentioned, the present inventors have uncovered that the electrospun scaffolds of the present invention are highly suitable for guiding bone or connective tissue formation and that such a scaffold can be used in bone and connective tissue regeneration and/or repair.

Thus, according to an additional aspect of the present invention there is provided a method of inducing formation of a bone or connective tissue, the method comprising seeding the scaffold with cells in a medium selected suitable for proliferation, differentiation and/or migration of the cells, thereby inducing formation of bone or connective tissue.

According to the teachings of the present invention and as illustrated in the Examples section which follows, scaffolds which are particularly suitable for bone or connective tissue regeneration include, but are not limited to, PCL/HA and/or PCL/gelatin/HA scaffolds.

As used herein, the phrase "connective tissue" refers to tissues which surround, protect, bind and support all of the structures in the body. Examples of connective tissues include, but are not limited to, cartilage (including, elastic, hyaline, and fibrocartilage), collagen, adipose tissue, reticular connective tissue, embryonic connective tissues (including mesenchymal connective tissue and mucous connective tissue), tendons, ligaments, and bone.

According to the teachings of the present invention various types of bones can be formed by the use of electrospun scaffolds, these include without being limited to, ethmoid, frontal, nasal, occipital, parietal, temporal, mandible, maxilla, zygomatic, cervical vertebra, thoracic vertebra, lumbar vertebra, sacrum, rib, sternum, clavicle, scapula, carpal bones, ilium, ischium, pubis, patella, calcaneus, and tarsal bones. The present invention also contemplates generation of long bones (i.e. bones which are longer than they are wide and grow primarily by elongation of the diaphysis with an epiphysis at the ends of the growing bone). Examples of long bones include femur, tibia, fibula (i.e. leg bones), humerus, radius, ulna (i.e. arm bones), metacarpal, metatarsal (i.e. hand and feet bones), and the phalanges (i.e. bones of the fingers and toes).

According to one embodiment, tissue formation is effected ex vivo—following which the scaffolds are implanted into the subject (e.g., a subject suffering from a pathology requiring tissue regeneration and/or repair as described hereinbelow). In such cases the cells seeded on the scaffold for ex vivo formation of a tissue can be derived from the treated individual (autologous source) or from allogeneic sources such as embryonic stem cells which are not expected to induce an immunogenic reaction.

Those skilled in the art are capable of determining when and how to implant the scaffold to thereby induce tissue regeneration and treat the pathology. The site of implantation is dependent on the disease to be treated. For example, if the pathology to be treated is a fractured bone the scaffold is seeded with MSCs or osteoblasts and following the required days in culture the scaffold is preferably implanted in the damaged bone tissue. The scaffolds of the present invention are suitable for ex vivo tissue formation to be utilized in orthopedic, periodontal, neurosurgical and oral and maxillofacial surgical procedures.

According to another embodiment, tissue formation is effected in vivo—in this case the scaffold supported cells are typically implanted into the subject immediately following seeding.

Since the scaffolds of the present invention may be used to generate tissue thereon, they may be used for treating diseases characterized by tissue damage or loss (e.g. bone or cartilage loss).

As used herein, the term "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, the phrase "pathology characterized by bone or cartilage damage or loss" refers to any disorder, disease or condition exhibiting a bone or connective tissue damage (i.e., non-functioning tissue, cancerous or pre-cancerous tissue, broken tissue, fractured tissue, fibrotic tissue, or ischemic tissue) or a bone or connective tissue loss (e.g., following a trauma, an infectious disease, a genetic disease, and the like) which require tissue regeneration. Examples for disorders or conditions requiring bone or connective tissue regeneration include, but are not limited to, bone cancer, articular cartilage defects, musculoskeletal disorders, including degenerative disc disease and muscular dystrophy, osteoarthritis, osteoporosis, osteogenesis, Paget's disease, bone fractures, and the like.

As used herein, the term "subject" refers to mammals, including humans. Preferably, this term encompasses individuals who suffer from pathologies as described hereinabove.

Methods of implanting scaffolds in a subject are known in the art (see for example, Artzi Z, et al., 2005, J. Clin. Periodontol. 32: 193-9; Butler C E and Prieto V G, 2004, Plast. Reconstr. Surg. 114: 464-73).

As mentioned, the cells which can be used according to the teachings of the present invention may comprise non-autologous cells.

Non-autologous cells (e.g. allogeneic cells or xenogeneic cells), such as human cadavers, human donors or xenogeneic donors (e.g. porcine), may induce an immune reaction when administered to the subject. Several approaches have been developed to reduce the likelihood of rejection of non-autologous cells. These include either suppressing the recipient immune system or encapsulating the non-autologous cells in immunoisolated, semipermeable membranes before transplantation.

Encapsulation techniques are generally classified as microencapsulation, involving small spherical vehicles and macroencapsulation, involving larger flat-sheet and hollow-fiber membranes (see for example, Uludag, H. et al. Technology of mammalian cell encapsulation. Adv Drug Deliv Rev. 2000; 42: 29-64). Pollok et al were able to successfully encapsulate a polymer scaffold seeded with islets using porcine chondrocytes [Dig Surg 2001; 18:204-210].

Methods of preparing microcapsules are known in the arts and include, for example, those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules may be prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents which can be used to minimize immunosuppression include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The electrospun scaffold supported cells of the present invention may be implanted to a subject per se, or it may be mixed with suitable carriers or excipients.

Hereinafter, the term "carrier" refers to a carrier or a diluent that does not cause significant irritation to an organism and does not abrogate the biological activity and properties of the scaffold. Exemplary carriers include Hank's solution, Ringer's solution, or physiological salt buffer.

Typically a therapeutically effective amount of scaffold supported cells are administered to the subject—i.e. an amount cells effective to prevent, alleviate or ameliorate symptoms of a disorder (e.g., bone or connective tissue disorder) or generate a therapeutic amount of tissue in the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce tissue regeneration (e.g. bone and cartilage formation). The minimal effective concentration (MEC) will vary for each preparation, but can be estimated from in vitro data. Dosages necessary to achieve the MEC will depend on individual characteristics and route of administration. Detection assays can be used to determine plasma concentrations.

The amount of scaffold supported cells to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is expected that during the life of a patent maturing from this application many polymers will be developed and techniques for electrospinning thereof and the scope of the term electrospun polymers is intended to include all such new technologies a priori.

As used herein the term "about" refers to ±10%

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of PCL Electrospun Scaffolds

Materials and Experimental Procedures
Electrospinning of Scaffolds

Poly (e-caprolactone) (PCL), a biodegradable polyester, with an average molecular weight of 80 kDa (Aldrich, USA) was dissolved in chloroform to obtain 10% wt. solution. The polymer solution was delivered at a constant flow rate to a metal capillary connected to a high voltage (13 kV). A fluid jet was ejected from the capillary. As the jet accelerated toward a grounded collector, the solvent evaporated and charged polymer fiber was deposited on a collector in the form of a non-woven scaffold. Hydroxylapatite (HA) particles (about 0.5 µm to 8 µm in diameter), dispersed in aqueous solution, were spread during the deposition process through a pneumatic setup located beyond the spinning apparatus (FIG. 2A).

The non-woven scaffold was cut in round shapes (0.5 mm) to fit a single well of a 96 well plate, sterilized (with oxygen plasma and antibiotics), washed (with PBS) and soaked with DMEM medium before cell seeding was carried out.

Cells, Culture Conditions and Analysis

Rat bone marrow mesenchymal stem cells (MSCs) were isolated and cultured on the electrospun scaffolds for up to three weeks in either basal control DMEM medium containing 15% FCS, 20 mM L-glutamine and Pen-Strep (100 U/ml, 100 µg/ml), or in a osteogenic medium additionally supplemented with 100 µg/ml ascorbic acid, 10 mM sodium β-glycerophosphate and $10^{-8}$ M dexamethasone. Bone marrow MSCs (250,000 cells per well) were cultured on the electrospun scaffolds in 96-well dishes. Samples were collected 0, 7, 14, 21 days following the beginning of incubation for the various tests.

The rate of cell proliferation was assessed by Alamar blue (Serotec, UK).

For imaging and visualization of the cells on the scaffolds, the cells were labeled for 24 hours with CFDA (Molecular probes) prior to imaging with a confocal microscope (Olympus).

Histology and Analysis

Selection of adherent osteoprogenitor cell subpopulation from MSCs was established by identifying the osteogenic cells using specific osteogenic cell markers (osteonectin, RNA of osteonectin, bone sialoprotein alkaline phosphatase and bone morphogenetic protein). The selected osteoprogenitor cells were further identified by osteocalcin immunoreactivity, positive Alizarin red S and von Kossa staining, and by alkaline phosphatase activity. Scaffold specimens were fixed in 4% formalin in 0.1 M phosphate buffer (pH 7.4) and stained with hematoxylin and eosin (H+E) for general morphology, with Alizarin red S for mineralized matrix and with osteocalcin for immunodetection of bone specific matrix proteins. Scaffold specimens were fixed in glutaraldehyde (for 24 hours), $OsO_4$ (for 1 hour), Tannic acid, dehydrated in graded ethanols, sputter coated with gold palladium and photographed by scanning electron microscope (SEM, 100 QT operating at 100 volts). Additional samples were sputter coated with carbon and examined by electron dispersive spectroscopy (EDS).

Results

Electrospun scaffolds revealed a 3-D structure of non-woven, randomly oriented fibers with diameters ranging between 100-400 nm and with HA particles integrated between the fibers (FIG. 1C).

Bone marrow-derived MSCs cultured on the electrospun scaffold for 7 days in medium containing osteogenic supplements revealed after 1 week a net-like arrangement of small cell clusters. The amount of cell clusters increased gradually after 2 weeks and up to three weeks in culture. Positive staining with alizarin red S indicative of mineralized bone matrix was observed in cell clusters on the scaffold after 2 weeks and after 3 weeks. MSC proliferation on the scaffold tested by Alamar blue assay, revealed gradual increase up to 7 days in both control and osteogenic media. Light microscopy and scanning electron microscopy (SEM) analysis demonstrated characteristic osteogenic condensation and cell cluster formation followed by changes in cell morphology. Energy dispersive spectroscopy (EDS) analysis proved the occurrence of extensive matrix mineralization. In vivo results in cranial defect animal model indicated enhanced cranial defect closure following osteogenic cell-construct implantation (data not shown).

Example 2

Generation of PCL/Gelatin Electrospun Scaffolds, Analysis and In Vivo Use

Materials and Experimental Procedures

Electrospinning of Scaffolds

PCL (approximately 80 kDa, Aldrich, USA) and acid Gelatin (Nitta Gelatin, Japan) were dissolved together (at a 1:1 ratio) in fluorinated alcohol of 2,2,2-trifluoroethanol (TFE) to give 9% and 12% solutions (w/v). The 9% solution was extruded from a 5 ml syringe connected to a hypodermic needle (bore size 0.6 mm; flow rate 3 ml/hr). The strength of the electrostatic field was 0.8 KV/cm. The electrospun nanofibers were deposited onto a grounded collector in the form of a non-woven sheet. Hydroxylapatite (HA) particles (about 0.5 μm to 8 μm in diameter), dispersed in aqueous solution, were spread during the deposition process through a pneumatic setup located beyond the spinning apparatus.

The end stage product size was 35×35×1.6 mm which was further cut into circular shapes (8 mm diameter) to fit into 24 well tissue culture plates. The specimens were sterilized by oxygen plasma prior to seeding of the cells.

Cell Source and Culture Conditions

Human bone marrow aspirates obtained under the guidelines of the Helsinki Committee for Human Ethics were used. Samples were washed twice in PBS (10 min at 1250 rpm). The cells obtained were centrifuged for 10 min at 1250 rpm, washed with fresh medium and subsequently re-suspended and plated in control DMEM medium containing 15% FCS, 20 mM L-glutamine and Pen-Strep (100 U/ml, 100 μg/ml), or in a osteogenic medium additionally supplemented with 100 μg/ml ascorbic acid, 10 mM sodium β-glycerophosphate and $10^{-8}$ M dexamethasone. The cells were incubated at 37° C. at 5% $CO_2$ for 10 days (P0) and were further expanded for an additional week (P1), trypsinized and re-plated in a-DMEM for another week (P2). At the end of passage 2, cells were trypsinized and seeded in the scaffold under rotating conditions (500,000 cells/scaffold) in 10 ml medium (in a 50 ml tube). A first portion of the scaffold seeded cells were examined for viability and a second portion was used for in vivo transplantation ($2\times10^6$ cells/scaffold).

Additional bone marrow-derived green fluorescent protein (GFP)-labeled MSCs were seeded in the scaffold ($1\times10^6$ cells/scaffold) and were further analyzed employing a fluorescence microscope, as described below).

Cell Viability Assay

Cell viability (after seeding in the scaffold) was assessed by the AlamarBlue™ Assay (Serotec, USA) according to the manufacturer's protocol. Briefly, cell-seeded scaffolds (500,000 cells/scaffold) were incubated (at 37° C.) with 10% (v/v) alamarBlue reagent in a-DMEM medium for 2 hours). Following incubation, data was collected using a FLUOstar Galaxy fluorometer. Fluorescence was recorded at 540 nm excitation and 580 nm emission and results were shown in arbitrary units means of 3 replicates and were subjected to statistics using student's T-test analysis.

Microscopic Analysis

Histology:

Following a 14 day incubation at 37° C. in a humidified environment containing 5% carbon dioxide, cell-scaffold constructs were processed as follows:

1. Scaffolds were visualized with a fluorescent microscope using the GFP-labeled cells-scaffold constructs.

2. At the end of the experiment, cells and scaffold fibers were detected under a light microscope using the following protocol: scaffolds were fixed with NBF (4% neutral buffered formalin −0.1 M phosphate buffer, pH 7.4), stained with hematoxylin and Eosin (H+E) and with Masson's trichrome.

Scanning Electron Microscopy:

For Scanning Electron Microscopy (SEM) studies, samples of pre-seeded scaffolds were acquired, as well as scaffolds containing cells 10 days after seeding in the dynamic flow culture. These scaffolds were fixed in glutaraldehyde (for 24 hours), in 1% OsO4 (for 1 hour) and in 2% tannic acid (for 10 minutes). Scaffolds were then dehydrated in graded ethanol solutions, sputter coated with gold palladium and photographed by scanning electron microscope, Jeol JSM-35 C operating at 15 kV.

Mechanical Properties

Fiber's Diameter:

The fiber's average diameter (measured prior to implantation) was found to be around 1-2 μm as measured using SEM.

Scaffold Porosity:

Scaffold porosity was estimated taking the sample's weight and dividing it by the material's (PCL/Gelatin 1/1) theoretical bulk weight for the same sample volume:

$$\frac{M}{m \cdot V} = \frac{0.362}{m \cdot (35 \cdot 35 \cdot 1.6)} =$$

$M$- Sample's weight [gr]

$m$- Polymer's theoretical specific weight [gr/mm$^3$]

$V$- Sample's volume [mm$^3$]

In Vivo Construct Evaluation

All procedures involving the use of animals were conducted in accordance with the guidelines of the Institutional Animal Ethics Committee of the Technion, Israel.

For the in vivo transplantation procedure, $2 \times 10^6$ cells were seeded in the scaffold. Athymic nude mice (7-weeks-old) weighing between 20-25 g were used. The osteogenic potential of the cell-scaffold constructs in ectopic subcutaneous animal model was tested for 8 weeks. Two cell-scaffold constructs were implanted in the backs of each mice and two scaffolds containing no cells (control group) were transplanted in the opposite side of each mice. The skin was than carefully sutured and animals were treated with antibiotics for 5 days.

Histology

After 8 weeks, samples designated for morphology were fixed with 10% neutral phosphate buffered formalin pH 7.2, decalcified (for 2 weeks) in 10% ethylenediaminetetraacetic acid (EDTA) in 0.1 M Tris-HCl buffer, pH 7.2, dehydrated in graded ethanol, embedded in paraffin, sectioned and stained with hematoxylin and eosin (H&E) and with Masson's Trichrome procedure for general morphology.

Results

Electrospun PCL/Gelatin/HA scaffolds revealed a 3-D structure of non-woven, randomly oriented fibers with diameters ranging between 0.3 μm-1.5 μm and with HA particles integrated between the fibers (FIGS. 3A, 4A-B). GFP-labeled osteoprogenitor cells seeded within the scaffold can be clearly seen (FIGS. 3B, 4C-D).

The GFP-labeled osteoprogenitor cells can be clearly seen in the scaffolds one week after cells were seeded in the PCL/Gelatin/HA scaffolds (FIGS. 6, 7A-C and 8A-B).

8 weeks following implantation of the electrospun PCL/Gelatin/HA scaffolds in nude mice, induction of bone formation was observed (FIGS. 5A-B). No bone formation was observed in the control specimens transplanted without the osteoprogenitor cells (data not shown).

Example 3

Generation of Scaffolds for Connective Tissue Regeneration

Bone marrow derived MSCs will be selected in culture for their chondrogenic lineage using chondrogenic markers (such as alcian blue staining and collagen type II immunohistochemistry). These cells will be seeded in the different electrospun scaffolds (as explained in detail in Example 2 hereinabove) and will be examined for their potential to form cartilage. Formation of cartilage will be examined in vivo in ectopi subcutaneous animal models and in joint cartilage defect.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A non-woven electrospun scaffold comprising polymeric nanofibers and a plurality of osteoconductive particles comprising hydroxylapatite (HA), wherein an average diameter of said polymeric nanofibers ranges from about 100 to 400 nm and whereas said osteoconductive particles are greater than 1 μm in diameter, wherein said polymeric nanofibers and a plurality of osteoconductive particles are concomitantly dispensed from two separate dispensers, and wherein said osteoconductive particles are situated between said electrospun polymeric nanofibers.

2. The scaffold of claim 1, wherein said polymeric nanofibers comprise biodegradable polymers.

3. The scaffold of claim 1, wherein said polymeric nanofibers comprise non-biodegradable polymers.

4. The scaffold of claim 1, wherein said polymeric nanofibers comprise biodegradable polymers and non-biodegradable polymers.

5. The scaffold of claim 1, further comprising a plurality of cells seeded within.

6. The scaffold of claim 5, wherein said cells are mesenchymal stem cells.

7. The scaffold of claim 5, wherein said cells are selected from the group consisting connective tissue cells, chondrocytes and osteoblasts.

8. The scaffold of claim 1, wherein a volume of the scaffold is greater than 1 mm$^3$.

9. The scaffold of claim 1, wherein the scaffold is a porous scaffold.

10. The scaffold of claim 9, wherein a pore of said porous scaffold comprises an average pore diameter of about 300 μm.

11. The scaffold of claim 1, further comprising at least one agent for promoting cell adhesion, colonization, proliferation, differentiation, extravasation and/or migration.

12. A method of fabricating a non-woven electrospun scaffold according to claim 1 comprising:

(a) dispensing within an electrostatic field from a first dispenser at least one liquefied polymer into a collector; and concomitantly (b) dispensing from a second dispenser a dispersion osteoconductive particles comprising HA into said collector, wherein said particles are greater than 1 μm in diameter, thereby fabricating a scaffold.

13. The method of claim 12, further comprising dispensing within said electrostatic field an adhesive agent from a third dispenser into said collector, wherein said dispensing is effected concomitantly with said dispensing from said first dispenser of said at least one liquefied polymer.

14. The method of claim 12, wherein said liquefied polymer comprises a biodegradable polymer.

15. The method of claim 12, wherein said liquefied polymer comprises a non-biodegradable polymer.

16. The method of claim 12, wherein said liquefied polymer comprises a biodegradable polymer and a non-biodegradable polymer.

17. A method of fabricating a non-woven electrospun scaffold according to claim 1 comprising:
   (a) collecting an electrospun polymer in a collector; and concomitantly
   (b) dispensing osteoconductive particles comprising HA into said collector, said particles being greater than 1 µm in diameter, thereby fabricating a scaffold.

18. The scaffold of claim 1, wherein an amount of said polymeric nanofibers per 1 mm$^3$ scaffold is less than 0.1 mm$^3$.

* * * * *